ated under 35

(12) United States Patent
Molgaard-Nielsen

(10) Patent No.: US 8,118,784 B2
(45) Date of Patent: *Feb. 21, 2012

(54) HAEMOSTATIC VALVE

(75) Inventor: Arne Molgaard-Nielsen, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/288,705

(22) Filed: Oct. 22, 2008

(65) Prior Publication Data

US 2009/0118681 A1 May 7, 2009

Related U.S. Application Data

(60) Provisional application No. 61/001,018, filed on Oct. 30, 2007.

(51) Int. Cl.
*A61M 5/178* (2006.01)
(52) U.S. Cl. .................................. 604/164.06
(58) Field of Classification Search .............. 604/249, 604/167.06
See application file for complete search history.

(56) References Cited

U.S. PATENT DOCUMENTS

| 2,590,215 | A | * | 3/1952 | Sausa | 138/45 |
| 4,642,833 | A | * | 2/1987 | Stoltz et al. | 15/1.7 |
| 4,673,393 | A |   | 6/1987 | Suzuki et al. | |
| 4,932,959 | A | * | 6/1990 | Horzewski et al. | 606/194 |
| 4,946,133 | A | * | 8/1990 | Johnson et al. | 251/149.1 |
| 5,071,411 | A | * | 12/1991 | Hillstead | 604/246 |
| 5,161,773 | A | * | 11/1992 | Tower | 251/5 |
| 5,176,652 | A |   | 1/1993 | Littrell | |
| 5,391,154 | A |   | 2/1995 | Young | |
| 5,556,387 | A | * | 9/1996 | Mollenauer et al. | 604/249 |
| 5,634,937 | A | * | 6/1997 | Mollenauer et al. | 606/213 |
| 5,653,697 | A |   | 8/1997 | Quiachon et al. | |
| 5,797,879 | A | * | 8/1998 | DeCampli | 604/93.01 |
| 5,807,312 | A | * | 9/1998 | Dzwonkiewicz | 604/30 |
| 5,819,801 | A | * | 10/1998 | Palffy | 137/826 |
| 5,895,376 | A | * | 4/1999 | Schwartz et al. | 604/256 |
| 5,913,847 | A | * | 6/1999 | Yoon | 604/523 |
| 6,152,933 | A | * | 11/2000 | Werp et al. | 606/130 |
| 7,118,086 | B1 | * | 10/2006 | Borglum et al. | 251/5 |
| 7,563,250 | B2 | * | 7/2009 | Wenchell | 604/167.01 |
| 2003/0130617 | A1 | * | 7/2003 | Leone | 604/82 |
| 2005/0038396 | A1 | * | 2/2005 | Claude et al. | 604/246 |
| 2005/0171479 | A1 |   | 8/2005 | Hruska | |
| 2008/0109028 | A1 | * | 5/2008 | Styrc | 606/194 |

FOREIGN PATENT DOCUMENTS

| DE | 112005001566 T5 | 5/2007 |
| EP | 0567141 | 10/1993 |
| WO | PCT/US2008/012284 | 3/2009 |
| WO | PCT /US2008/012284 | 3/2009 |

* cited by examiner

*Primary Examiner* — Kevin C Sirmons
*Assistant Examiner* — Andrew Gilbert
(74) *Attorney, Agent, or Firm* — Richard J. Godlewski

(57) ABSTRACT

The haemostatic valve assembly (10) includes a housing (14) with a chamber (16) therewithin. A flexible valve element (26) is located in the chamber (16) and supported by the housing (14). A source (28) of pressurized fluid can be fed into the chamber (16) through a port (18) in the housing (14). A catheter, dilator, pusher or other elongate insert fed through the haemostatic valve assembly (10) can be sealed by the application of fluid pressure into the chamber (16), which causes the sides of the valve element (26) to press against the insert (24) thereby to provide an effective seal.

15 Claims, 6 Drawing Sheets

HAEMOSTATIC VALVE

CROSS-REFERENCE TO RELATED APPLICATIONS

This application claims priority of provisional application Ser. No. 61/001,018, filed Oct. 30, 2007.

TECHNICAL FIELD

The present invention relates to a haemostatic valve assembly, to an intraluminal introducer, to a deployment device, and to an endoluminal treatment or diagnosis assembly.

BACKGROUND OF THE INVENTION

There are now well established techniques for carrying out endoluminal treatments and diagnoses on a patient. A diagnosis may, for example, involve injection of contrast material and saline solution, A treatment may, for example, involve insertion and deployment of implants or prostheses for carrying out of surgical procedures. It may also or in the alternative involve insertion, use and removal of catheters or tools, such as angioplasty or moulding balloons. A treatment may also involve injection of contrast material, saline solution, administration of medicaments and so on. The treatments and diagnoses can be effected within a patient's vascular system, such as arteries or veins. They can also be carried out within other bodily tubes which carry pressurized fluids, examples being the bilary tree and urological system, as well as within an organ, such as the cerebral ventricles and so on.

Endoluminal deployment or treatment devices typically include an elongate catheter assembly having an outer sheath and an internal dilator tip for insertion into the vasculature of a patient up to the deployment or treatment site and into which an elongate treatment or deployment element can be inserted. For example, the sheath may house a catheter or pusher element for carrying a medical device to be implanted into the patient. The sheath may also carry elongate tool elements, catheters for administering medicaments and so on. In the course of such treatments or diagnoses it is important to ensure that the patient does not suffer blood loss through the sheath. For this purpose, it is known to provide at the proximal end of introducer one or more haemostatic valves in series to close off leakage through the outer sheath.

These haemostatic valves must be such that they allow sliding movement of any delivery or treatment element within the sheath and also for the removal and replacement of such elements. The latter is important, for example, in that many medical procedures may require a plurality of different elements to be passed through the sheath at different times of the procedure for location at a specific position in the patient. Normally, when an exchange of devices takes place, the haemostatic valve has both to seal and allow movement of devices with a diameter up to the inner diameter of the sheath, much smaller devices such as a wire-guide typically of 1 mm or so, as well as to seal when the sheath is empty.

Typically, in any one assembly there is provided a variety of valves in light of the difficulties in achieving a reliable seal, all while providing for the removal and replacement of the inserted elements.

Some of these valves are in the form of a disk of elastomeric material located at a proximal end of the sheath and within which there is provided a cut, straight or more commonly Y-shaped, through which an element can be inserted so as to be located within the sheath. As such valves do not provide a complete seal when they hold an insert, typically allowing leakage between the slit and the insert, so it is common to provide a plurality of such valves in series with one another. These are either at different angular rotations relative to one another or are of different designs, so that collectively they provide a reasonably reliable seal. Typically, there will also be provided one disc with a round hole, optimal for the most-used diameter of a device which passes through that particular sheath. The round disc will give a certain friction, depending upon the need for a forceful seal or to accommodate the size of the actual device passed therethrough.

Examples of such valves can be found, for instance, in U.S. Pat. No. 4,673,393, U.S. Pat. No. 5,176,652 and US-A-2005/017,479.

A difficulty arises with the use of a series of seals, however, in that in order to have good sealing characteristics they also tend to create a significant resistance to movement of an insert, which can substantially impair the operability of the insert by making it too hard to slide within the sheath. This can in some instances lead to damage of the insert, for example by kinking. This risk is particularly acute for inserts which are by necessity very flexible or of a small diameter.

In order to mitigate the above disadvantages, it is also known to use a haemostatic valve which can be opened and closed under the clinician's control. This has the advantage that an element can be inserted into the sheath and moved therealong with relative ease while the controllable haemostatic valve is in an open configuration. Once the insert is in place the valve can be tightened to seal. Such tightening is also advantageous during the procedure of insertion of the device in the sheath assembly. In practice, it is often necessary for such a solution also to include a valve which self-seals, such as one or more of the disk-shaped valves mentioned above to secure sealing during handling.

Such selectively openable and closable valve elements typically have an elongate valve member of tubular form which can be closed by twisting or by application of pressure laterally on the valve element by means of one or more movable closing plates.

Examples of such selectively sealable haemostatic valve assemblies can be found, for example, in U.S. Pat. No. 5,391,154 and U.S. Pat. No. 5,653,697.

A problem with such selectively sealable haemostatic valve assemblies is that they require an additional operation to be performed by the clinician during the surgical procedure, that is the opening and closing of the valve element. This can be particularly disadvantageous during any medical procedure, where the clinician is typically required to perform several other tasks.

SUMMARY OF THE INVENTION

The present invention seeks to provide an improved haemostatic valve assembly and an improved intraluminal treatment or deployment device.

According to an aspect of the present invention, there is provided a haemostatic valve assembly including a chamber able to be pressurized, an elongate resiliently deformable valve element located within the chamber, a passage through which an elongate element can pass, the valve element being located so as to envelop at least a part of the passage, and means for supplying pressurized fluid to within the chamber, wherein pressurization of the chamber causes the valve element to be biased towards a closed position.

In practice the valve element is biased to a sealed configuration, at least when an element is located in the valve assembly.

In some embodiments, the valve element closes, that is gets smaller in its open diameter, around at least a part of the passage.

In the preferred embodiment, the valve is axially biased towards a closed position, that is towards the axis of the passage.

In an embodiment, the deformable valve element is fixed to at least one end of the chamber. Preferably, the valve element is fixed at both ends.

Advantageously, the chamber provides a substantially constant volume for pressurization fluid. It is also envisaged that the chamber could be or include a variable volume element such as an expandable volume or expansion chamber.

In practice, fluid can be supplied into the chamber and pressurized as desired. It will be appreciated that the fluid can be a gas or a liquid or any other material which exhibits fluid-like qualities. This pressure causes the deformable valve to be biased into a sealing condition against various different cylindrical devices, dilators or guide wires therein, or to a closed position, thereby to provide the desired seal in all of the operating states of the valve assembly. The advantage of the system is that the pressurized fluid can provide a reliable seal without requiring a large force to be applied to the seal and thus to any insert held within the valve element. In the case of a generally tubular valve element, the pressure applied to the valve can achieve reliable sealing both when the largest or the smallest inserts are placed therein as well as when any such insert is completely removed from the sheath and the chamber. Since the sealing force need not be large as a result of the substantially constant biasing force applied by the pressurized fluid, the force required to slide inserts through the closed or just sealing valve as it is closed towards the insert valve can be much less than with prior art devices. Furthermore, the pressure may be adjusted to provide an optimum seal at the various sizes of device in use at any particular moment.

Another advantage of this valve arrangement is it can seal along a greater longitudinal extent of a device in the valve assembly compared to prior at valve arrangements and can adjust within a span of sizes along the length in the valve element as well as according to the applied pressure.

In a preferred embodiment, without pressure or with a negative pressure the device preferably provides a fully open passage without any edges or other elements that could snag on the inserted device.

Yet another advantage of the assembly is that it provides a sealing operation which does not involve a mechanical twisting or pushing action, the latter being susceptible to incorrect operation and to over adjustment, which in some cases can result in the breakage of the sealing function.

The ability to adjust the pressure of the valve assembly provides an additional advantage of being able to optimize the resultant friction through the valve element by choice of the sealing pressure.

In the preferred embodiment, there is provided a source of pressurized fluid external to the chamber. Most preferably, the source of pressurized fluid includes a piston operated device for urging fluid into the chamber by movement of the piston.

Advantageously, the source of pressurized fluid includes a syringe coupled to a port of the chamber.

The chamber may include a compliant part that may allow movement within a range of sizes of the valve element without the need for adjusting the pressure with a piston or a syringe.

Another embodiment provides a pressure coupling between a blood vessel of the patient or from a fluid source, such as a saline fluid source, to the chamber. This could be a connection from the sheath to the outer chamber directly or by transmitting pressure via a membrane. Thus, the patient's blood pressure or the other fluid source would provide a self-regulating source of pressurized fluid into the chamber. This would give a self-adjusting sealing force when a device is located in the passage in the sheath, in which case there is no need for additional sealing and the sealing pressure is low because of lack of backflow. By contrast, when there is no device held in the valve assembly, the sheath is empty and there is a high backflow, thereby a higher pressure for sealing.

In all of these embodiments, the chamber can be pressurized at the start of the medical procedure with no further intervention normally being required. Thus, not only can this valve assembly provide a better sealing arrangement but one which is also simpler to implement.

The resiliently deformable valve is in one embodiment of a cylindrical or an hourglass shape and extends substantially across the entirety of the passage through the chamber. In one embodiment, the chamber is cylindrical and the valve element preferably in the form of an elastic cylindrical tube which is held in the pressurized chamber in an hourglass shape, giving easy passage at the ends and a seal at the middle to seal against any devices positioned or passed through the valve. The longitudinal shape with the ends being wider than the diameter of a device in the valve gives a relatively low friction compared to the sealing function.

In another embodiment, the valve extends over only a portion of the passage of the chamber. In this embodiment, it is preferred that there is provided means for securing the free end of the valve. This has the advantage of ensuring that the valve element is not undesirably deformed during insertion and removal of an element therein, such as protection against eversion of the valve. The securing means may include at least one filament.

In an embodiment, the valve is provided with an opening into the passage within the chamber. An additional advantage of this feature, over an above the advantages already mentioned, is that fluid used to pressurize the chamber can pass into the passage and therefrom into the sheath and thus into the patient. This can be a very efficient way of administering to the patient fluids used during treatment, such as saline solution, medicaments and so on, thus having the advantage of acting both as a sealing means and as a supply of such fluid during insertion and/or removal of the element in the passage of the valve.

In one embodiment the valve has a multi-leaflet form. Preferably this is a tri-leaflet valve.

Advantageously, the source of pressurized fluid is a regulated source so as to allow for variation and control of the valve closing pressure produced by the fluid.

According to another aspect of the present invention, there is provided a deployment device including a haemostatic valve assembly as specified herein.

According to another aspect of the present invention, there is provided an intravenous treatment assembly including a haemostatic valve assembly as specified herein.

BRIEF DESCRIPTION OF THE DRAWING

Embodiments of the present invention are described below, by way of example only, with reference to the accompanying drawings, in which.

DETAILED DESCRIPTION

Figure 1:
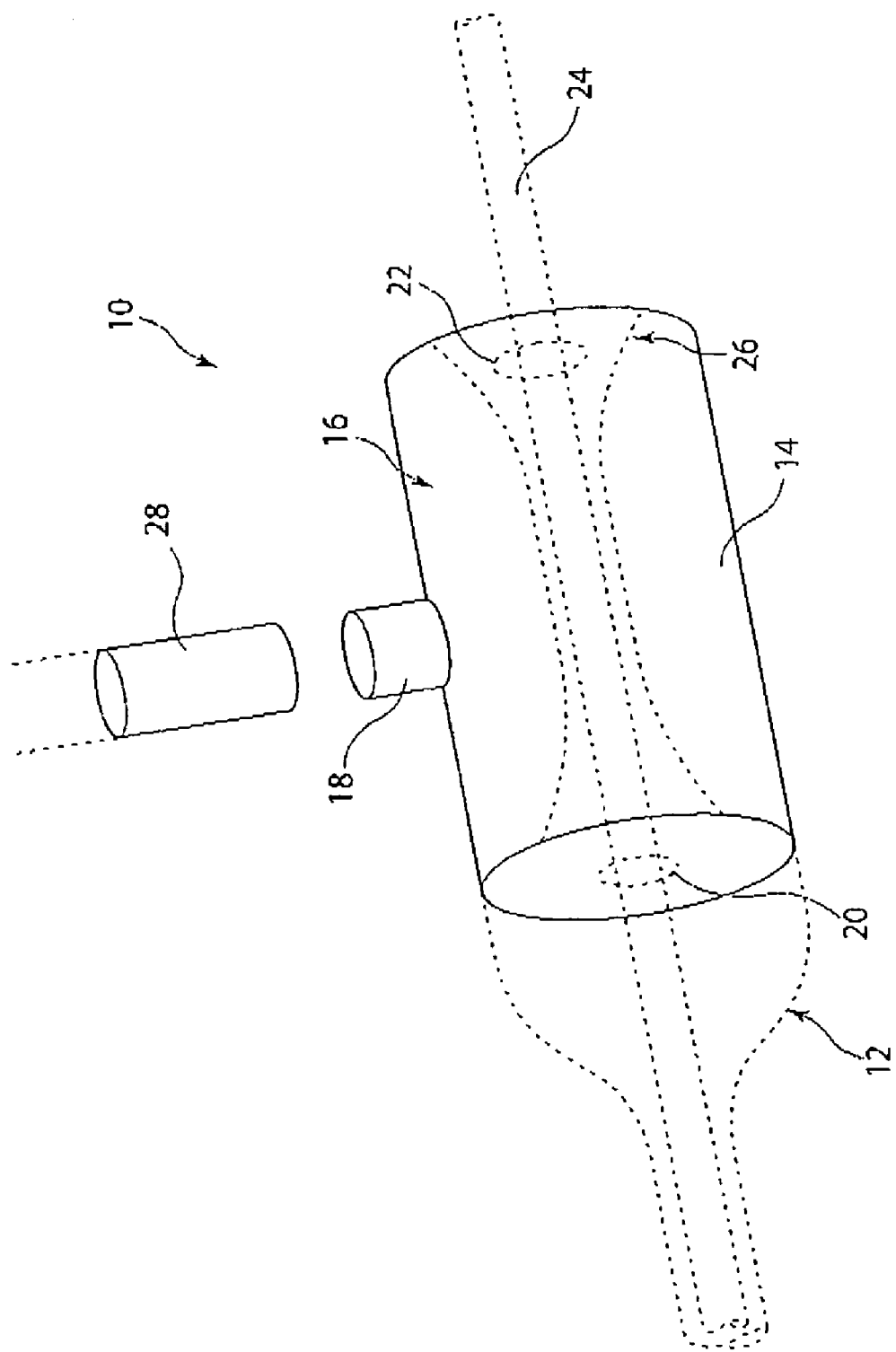
FIG. 1 shows in schematic form a perspective view of an embodiment of haemostatic valve assembly.
Figure 2:
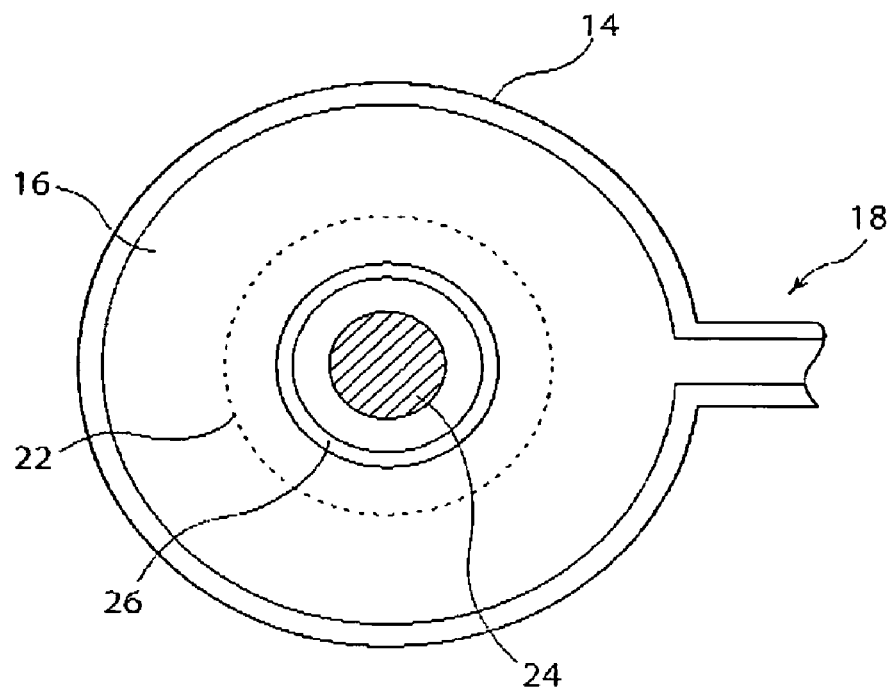
FIG. 2 is a transverse cross-sectional view of the assembly of FIG. 1.

Referring to FIGS. 1 and 2, there is shown in schematic form an embodiment of haemostatic valve assembly 10 which forms part of an introducer or deployment device for delivering devices to be inserted into a patient, for carrying out endoluminal placement of implants or for other endoluminal treatments known in the art. The introducer or deployment device could also be of any type designed to effect such delivery, diagnosis or treatments within a patient's organ containing fluids, where sealing during operation is advantageous. Such deployment devices are well known in the art and available, for example, from the applicant, particularly for the deployment of stents, stent grafts, vena cava filters, occlusion devices and so on. There is therefore no need to describe these devices in detail herein.

The valve assembly 10 is designed to couple in a fluid tight manner to a sheath assembly 12 of the deployment device, in a manner similar to existing haemostatic valve assemblies.

The assembly 10 includes a housing 14, preferably translucent, of generally cylindrical form in this embodiment, which provides a chamber 16 therewithin. The shapes of the housing 14 and chamber 16 are not important although it is preferred that they are both generally round in axial cross-section. The housing 14 also includes a port 18 for the introduction of pressurization fluid into the chamber 16.

In this embodiment, the housing 14 is provided with circular holes 20, 22 at either end thereof, although again the shape of the holes is not critical. These holes 20, 22 allow for the passage of a catheter or other insert 24 therethrough, one being shown in dotted outline, and are of such a size that they are able to accommodate inserts 24 of the maximum size the sheath 12 can accept.

A flexible valve element 26 is located within the chamber 16 and in this embodiment is supported by the housing 14 at each end thereof. In this embodiment, the valve element 26 is cylindrical and stretched or pressurized to be of a waisted or hourglass shape. The valve element 26 seals the chamber 16 from the holes 20, 22, thereby providing a passage from one hole 20 to the other hole 22 which is completely sealed from any fluid in the chamber 16.

The valve element 26 is fixed to the inner surfaces of the housing 14 by any suitable means including gluing, heat sealing or by any mechanical fastening.

In the preferred embodiment, the valve element can be formed from one or more sheets of a thin compliant material, such as polyurethane, silicone, polychloroprene (Neoprene), styrene butadiene, styrene ethylene butadiene, latex, a rubber or rubberized material.

The port 18 couples to a source 28 of pressurized fluid, which may include a syringe filled with a suitable fluid, a drop bag with fluid at a height giving a suitable pressure or a pump coupled to so as pump a suitable fluid from a supply. Described below are embodiments in which pressurization is effected by means of a coupling to a patient's blood back flow in the sheath in the vessel.

The fluid may be water, saline solution, blood or any other suitable fluid including a gas or any safe air at a set pressure which gives a good compliance to selected sizes.

Figure 3:
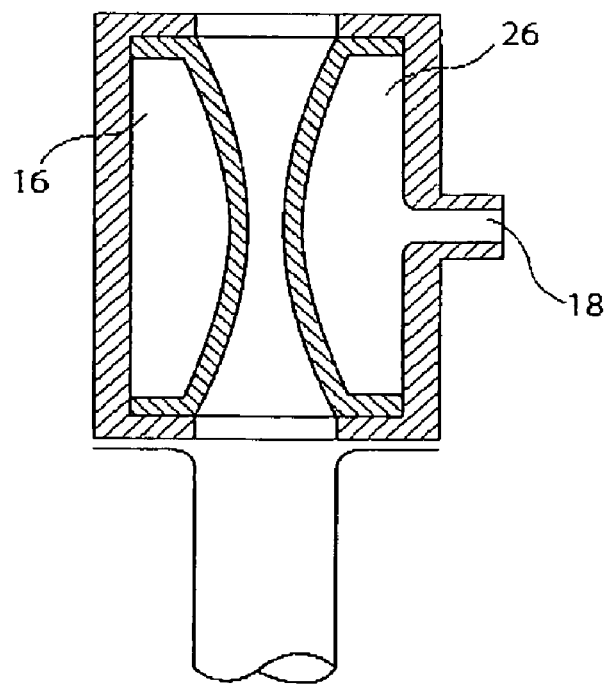
FIG. 3 shows in schematic form the valve and pressurization part of the assembly of FIG. 1.

FIG. 3 shows in schematic form a cross-sectional view in side elevation of the valve assembly 10 of FIGS. 1 and 2 useful in understanding the operation of the valve element 26.

When pressurized fluid is supplied through the port 18 into the chamber, this fluid applies a constricting force in all radial directions around the valve element 26 towards the axial centre of the device 10. This causes the valve element 26 to constrict, particularly at its centre or waist, which is furthest from the fixing points to the housing 14. This causes the valve element 26 to close around the passage 30 within the valve element 26 and between the two end holes 20, 22 in the housing 14. In practice, this force can cause sealing around big or small cylindrical elements or uneven shapes, or even complete closure of the passage 30 without any insert 24 being located therewithin. This is achieved by sufficient compression of the sides of the valve element 26 such that they eventually come into a central sealing configuration. The elasticity of the valve element 26 will enable it to close completely or almost completely, in dependence upon the pressure in the valve.

In the embodiment of FIGS. 1 to 3, as well as the other embodiments depicted in the other Figures, the valve 26 is located in the housing 14 substantially coaxially with the axis of the holes 20, 22 and is such as to close coaxially around the passage 30.

In practice, there is normally always provided an insert 24 within the valve assembly 10, such as an implant, a pusher or dilator or a guide wire, a diagnostic device, medical tools and the like. The valve element 26 seals against all such inserts, providing a reliable seal both when the insert is introduced as well as during its movement in the valve assembly 10. Moreover, as the seal provided by the pressurized fluid is a much more efficient seal than that provided by prior art systems, it is possible to provide a reliable seal without having to impart a large sealing force against the insert 24. In particular, it will be appreciated that the waist portion of the seal 26 will extend for a certain distance along an insert 24 placed in the valve which will be greater than the longitudinal sealing extent of a standard flat or pinched valve. Thus, the insert 24 can be fitted through and slid along the valve assembly 10 significantly more easily than with prior art devices.

In use, the clinician will pressurize the chamber 16 by application of the external pressure source (the syringe or pump, for example) via the port 18. This is preferably carried out before the delivery device is introduced into the patient.

Any fluid pressure from the patient's lumen in which the distal end of the deployment device is fed, caused primarily from patient's blood pressure tending to open the valve element 26, will be countered by the closing pressure from the pressurized fluid within the chamber 16 as the area outside the valve is larger than that of its inner surface.

It is preferred that the surgeon is provided with the ability to regulate pressure inside the chamber 16 and therefore the sealing pressure of the valve element 26. This can be achieved in its simplest form by tactile sensation on a syringe plunger. In another embodiment, the system may be provided with a pressure meter, which could be provided within the assembly 10 but which in another embodiment is provided as a separate element coupled within the pressurized fluid supply path. In the case where the pressurization fluid is provided by the patient's own blood supply, this alternative does not require regulation because it could be considered to be effectively self-regulated by the blood pressure in the sheath. In this regard, an open sheath without device held therein gives easy flow with high pressure and therefore provides a good sealing force. When a device is located in the sheath, the sheath could be described as almost filled, giving a lower sealing force but no need for a tight seal.

In addition, the pressure of the fluid used to close the valve 26 can be varied as desired to take into account different insert sizes and to optimize the function and sealing characteristics of the valve assembly. This is a feature which is not possible with prior art devices.

For the avoidance of doubt, with all the pressurization systems disclosed herein, the valve element 26 will close when pressure is applied thereto, even when there is no insert 24, for the reason that the effective pressure applied to the external surfaces of the flexible valve element 26, even at its waisted portion, will be greater than that applied to the internal surface (that is surface facing the chamber 16 as opposed to the surface facing the internal passage), due to the greater surface area of the external surfaces of the valve relative to their opposing internal surfaces. Thereby, the resultant pressure on the valve element 26 will be in a closing direction, as long as the absolute pressure within the chamber 16 is substantially not less than the absolute pressure within the housing 14 on the inside of the flexible valve member 26.

Thus, in the preferred embodiments, once the surgeon has pressurized the chamber 16, the surgeon can carry out the other medical procedures without having to readjust the seal assembly 10, which provides an automatic and continuous seal. Of course, in some embodiments it is envisaged that the surgeon may wish to reduce the pressure within the chamber 16 to facilitate further the insertion, or to raise the pressure on removal of insert 24, which could be done relatively easy by appropriate movement of the piston of a syringe providing pressurized fluid or by control of a pump where this is provided.

It is also envisaged that there may be provided a bleed of conventional form between the source of pressurized fluid and the port 18 on the valve assembly 10.

A closure valve (not shown) is preferably placed between the syringe and the camber to maintain the desired pressure.

In FIGS. 1 and 2 (as well as the other embodiments described below) the case 14 is of a substantially rigid construction, that is it is of a substantially fixed volume. However, it is envisaged that in some embodiments the casing 14 could have some flexibility thereto to provide a varying volume. In other embodiments, there may be coupled to the casing 14 an expansion chamber, which can be of conventional design so is not shown or described in detail herein.

Figure 4:
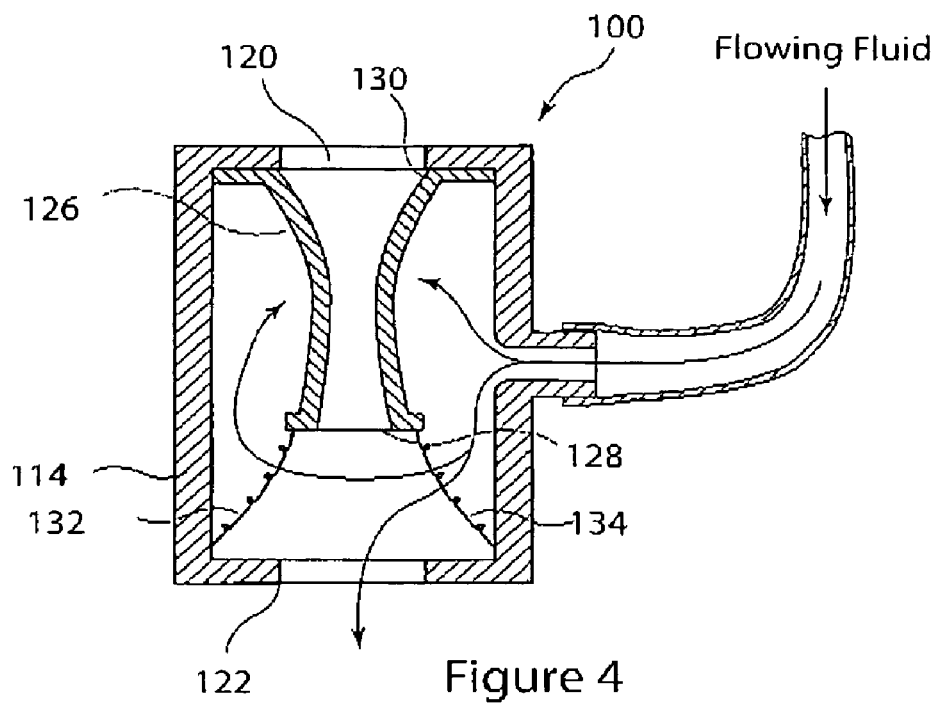
FIG. 4 shows in schematic form another embodiment of valve element.
Figure 5:
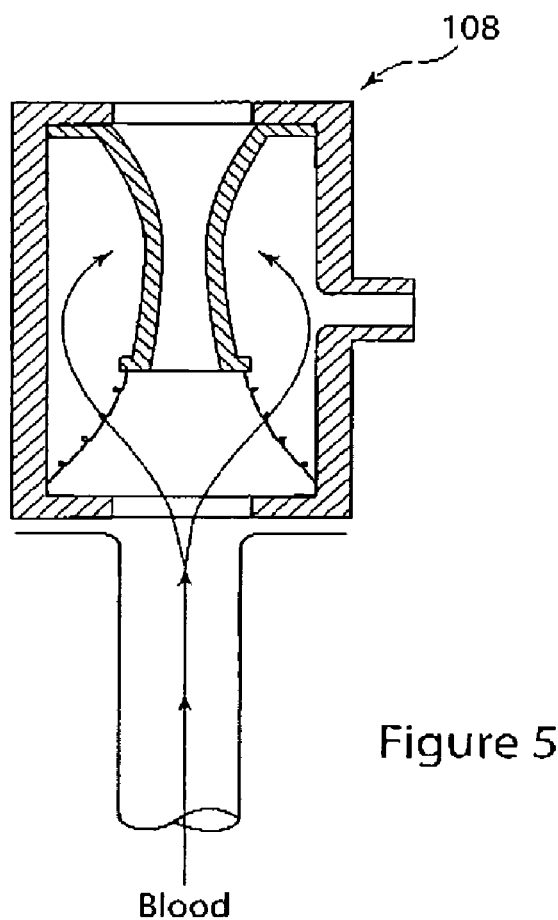
FIG. 5 shows another pressurization arrangement for a valve similar to that of FIG. 4.
Figure 6:
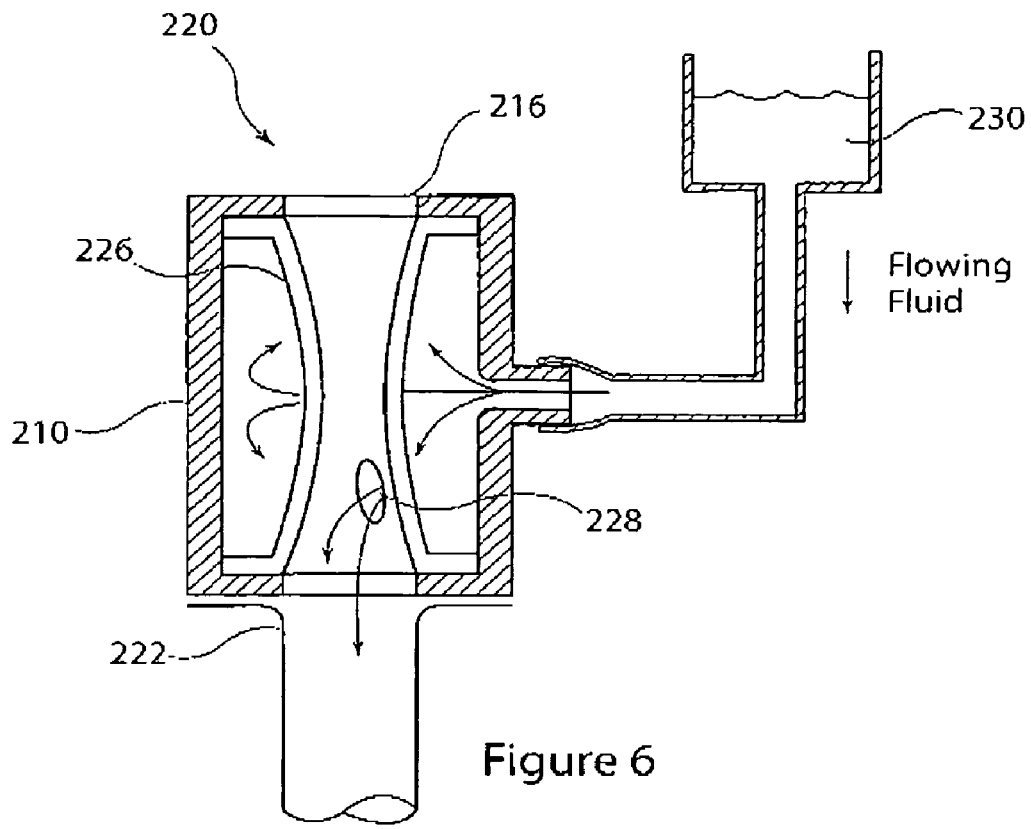
FIG. 6 shows in schematic form another embodiment of valve element.

FIGS. 1, 2 and 3 show a flexible valve element which extends continuously from one end of the casing 14 to the other, in effect completely sealing the chamber 16 from the passage between the holes 20, 22. It is not, however, essential to provide a complete seal between the chamber 16 and the passage 30. FIGS. 4 to 6 show alternative designs of flexible valve element 126 and 226 and means for pressurizing these into a sealing condition.

In the embodiment of FIG. 4, the valve element 126 extends to just beyond halfway in a longitudinal direction of the casing 114 and includes a narrow open end 128 and a larger upper end 130 which is fixed to the casing 114 and which surrounds the hole 120.

Optional tethers 132, 134 (two being shown but of which any suitable number could be provided) tie the end 128 of the valve element 126 to the opposite end of the casing 114, adjacent the hole 122. These tethers assist in preventing eversion of the valve element 126 as a catheter, pusher or other insert 24 is passed through the valve assembly 100.

As explained above, since the surface area of the outside of the valve element 126 is greater than that of its inner surface, pressure applied within the chamber 116, from pressurized fluid 28 fed through the portal 18, will naturally cause valve element 126 to constrict at its open end 128 and therefore to provide a sealing action against a catheter, pusher or other insert 24.

The embodiment of FIG. 4 is useful in that it can allow the valve assembly 100 to be used also as a supply of fluid to the patient, such as saline solution, medicaments or any other fluid used during the medical treatment or diagnosis, as shown by the arrows in FIG. 4. In this case, it can be advantageous to design valve element 126 such that its end 128 does not seal completely when there is no insert 124 within the valve assembly 100, in which case there is a passage of fluid through the port 18 and the end 128 into a patient's vessel or organ via the delivery device and in particular within the outer sheath 12 which in practice is coupled to the valve assembly 100.

FIG. 5 shows an example of arrangement in which the valve assembly 100 is coupled such that blood from the patient flows through the interstitial space between the sheath 12 and any insert 24 therein, around the openings or tethers 122, 134 and into the chamber so as to pressurize the valve 126 into a closed condition. Thus, in this embodiment, it is the patient's blood pressure in the sheath which gives the pressure for operating the valve.

It is envisaged that this solution will not require any additional pressure regulation system as it can rely upon self-regulation from the patient's blood pressure. It is not, however, excluded that in some instances additional regulation, such as a syringe or pump, might be provided.

Referring now to FIG. 6, there is shown a valve element 226 which is of similar shape to the valve element of the embodiment of FIGS. 1 to 3 and which extends fully between holes or openings 220, 222 in the casing 210. The difference between the valve element 226 of this embodiment and the valve element 26 of the embodiment in FIGS. 1 to 3 is that the valve element 226 provided with at least one opening 228 therewithin, to provide a passage for fluid between the chamber 216 and the interior of the valve element 226. This has the same purpose as the design of valve element 126 shown in the embodiment of FIG. 4.

Both embodiments of FIGS. 4 to 6 can be particularly advantageous when the patient's blood supply is used to provide the pressurized fluid into the chamber 116, 216. For this purpose, there is created in effect a closed path for blood from a patient which can create the necessary pressure to close the valve 126, 226.

FIG. 6 shows a fluid bag 230 for providing the source of pressurized fluid to operate the valve element 226. The fluid used will typically be a saline solution. The height of the bag 230 relative to the housing 210, which is preferably adjustable, will determine the pressure of the fluid in the housing 210 and therefore the closing pressure applied to the valve 226. Any leak in the valve will only leak out saline solution from the drop bag 230 into the sheath.

In this particular embodiment, the holes 228 in the valve 226 provide for passage of saline solution therethrough which thus to provide not only a source of pressurization fluid to close the valve 226 but also a source of saline solution to the patient. The number and size of the holes 228 in the valve 226 gives the maximum allowed flow of leaking fluid into the sheath.

The drop bag 230 could be used with all of the embodiments of valve structure. Moreover, the valve 226 could be used in place of the valve 126 in the embodiments of FIGS. 4 and 5.

Figure 7:
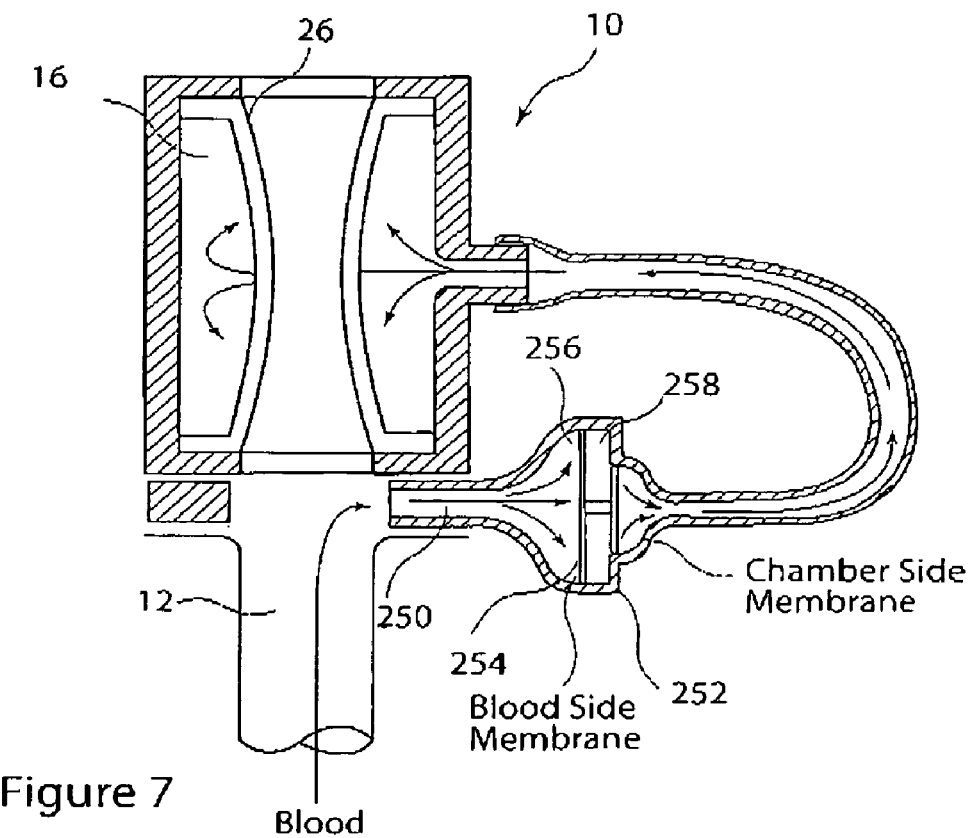
FIG. 7 shows another pressurization arrangement for such valve assemblies.

FIG. 7 shows an arrangement which uses a patient's own blood pressure for pressurizing the valve 26. A coupling 250 to the patient's blood system via the sheath 12 passes to a chamber 252 which is divided in two by a flexible membrane 254, that is a into blood side 256 and a chamber side 258. Fluid is contained in sealed manner in the chamber side 308 and chamber 16.

Blood pressure biases the membrane 204 towards the chamber side, thereby pressurizing the fluid in the chambers 258 and 16 to close the valve 26.

It will be appreciated that in this embodiment, there is no blood from the patient which is passed to the outside of the valve element 26, that is into the chamber 16. The patient's blood flow serves only to move the flexible membrane 254 so as to regulate pressure within the chamber 16. As described above, since the outer surfaces of the valve element 26 have a greater surface area than its inner surfaces, there would be a greater force applied on the outside of the valve 26 by the patient's blood pressure, thereby causing the valve 26 to be biased closed.

Figure 8:
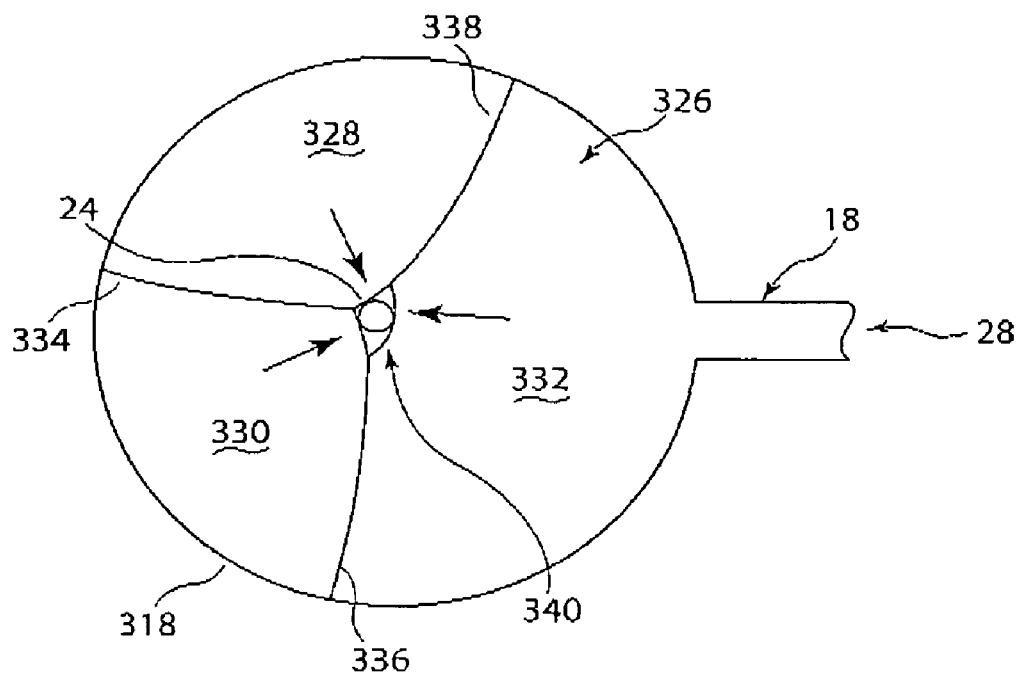
FIG. 8 shows a plan view of an embodiment of tri-leaflet valve element.

FIG. 8 shows in plan view an embodiment of valve structure useful for any of the valves shown in FIGS. 1 to 4 or any other valve configuration having the characteristics of the valves of those Figures. FIG. 8 shows valve element 326 being formed of three leaflets 328, 330 and 332. These are in effect elongate sheets of valve material which are sealed to one another at longitudinal seals 334, 336 and 338, thereby to create a valve element 326 having the general hourglass shape shown in the preceding Figures. The three valve material sheets are sealed against the housing 18 to make a tight connection to the holes 20 and 22. As can be seen in the plan view of FIG. 8, this structure of valve element 326 provides a triangular passage 340 through the valve element 326 and thus through the valve assembly 310. The advantage of this structure, it has been found, is that when pressure is applied to close the valve element 326, as shown by the arrows in FIG. 8, the three leaflets are able to close more tightly around the insert 24 than a valve element having, for example, two leaflets. Moreover, when compared to a valve element formed of a single leaflet, when a tri-leaflet valve element of the type shown in FIG. 8 is in its non pressurized state, there remains little contact between the leaflets 328-332 of the valve element 326 and the insert 24, thereby reducing any friction between these two components. This thus facilitates the movement of the element 24 through the valve assembly 310 which is, of course, an important advantage with deployment devices of the type contemplated in this application.

The embodiment of FIG. 8 can have any of the features of the valve elements 26, 126 and 226 shown in the preceding Figures. It is also envisaged in some embodiments that the valve element 386 may only have a tri-leaflet structure part way along its length, that is at its central portion.

Figure 9:
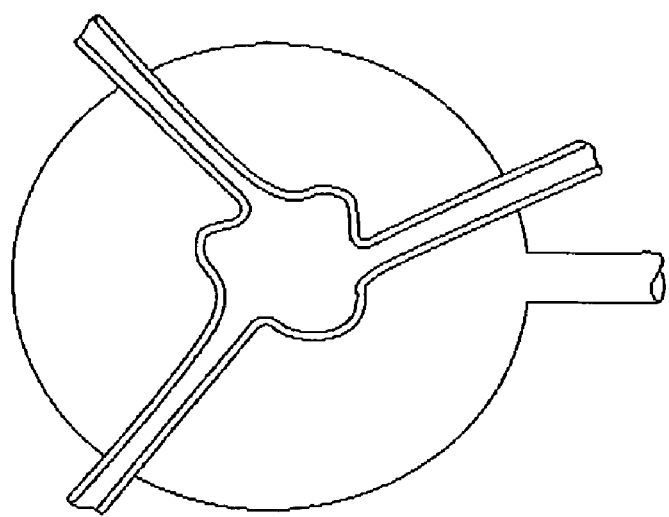
FIG. 9 shows the valve element of FIG. 9 in a sealed state.

In operation, the three leaflets 328-332 would come in sealing contact with one another by folding over themselves and/or over one another, as can be seen in FIG. 9.

Further details of a suitable structure for this tri-leaflet valve of FIGS. 8 and 9 can be found in the Applicant's copending U.S. Provisional patent application No. 60/001,019 filed on 30 Oct. 2008 and the United States Utility patent application claiming priority therefrom.

It is envisaged that this tri-leaflet valve element 326 could be pre-twisted, for example during manufacture, which can assist in its closure.

Figure 10:
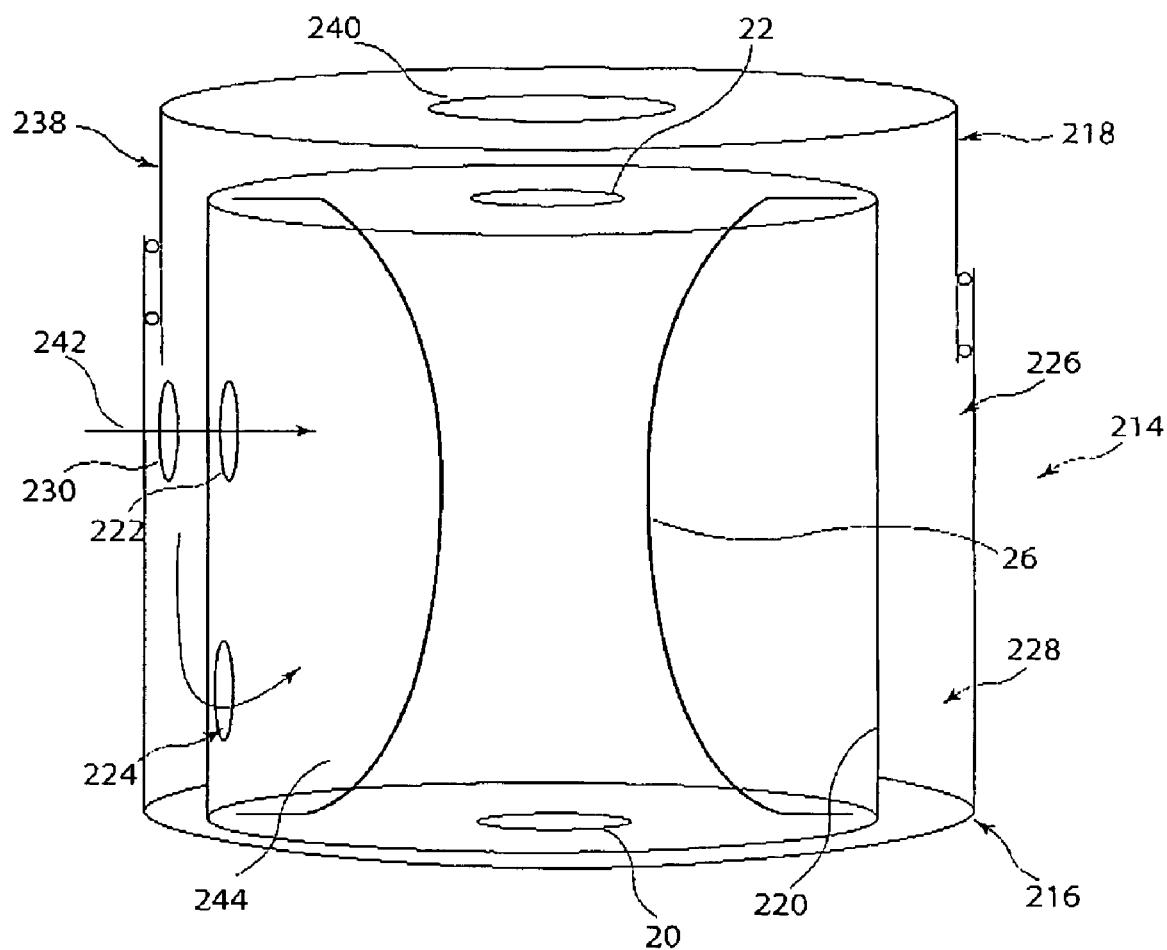
FIG. 10 shows another embodiment of valve assembly.

Referring now to FIG. 10, there is shown another embodiment of housing 214 for use in place of the housing 14 and 114 described above. The chamber 214 is formed of two parts 216, 218 which are able to nest one within the other in a fluid-tight manner. More particularly, the lower part 216, as viewed in FIG. 10, has a generally cylindrical casing 220 within which the valve element 26 is located as in the above-described embodiments. The cylindrical wall of the casing 220 is provided with first and second holes 222, 224. The part 216 is also provided with an outer cylindrical wall 226 co-axial with the casing 220 and sealed at one end by a lower annular wall between it and the casing 220. The other end of the wall 226 is open, providing an annular space 228 between it and the casing 220. The wall 226 is provided with one hole 230 which is aligned with the hole 222 in the inner casing 220, as can be seen in FIG. 10.

The upper part 218 is provided with an annular depending cylindrical wall 238 which nests into the space 228, preferably in a substantially fluid tight manner, and also has a hole 240 in its upper wall aligned with the holes 20, 22 in the casing 220 for the passage of a catheter therethrough. The hole 240 is preferably larger than the holes 20, 22.

During sterilization and delivery, the upper part 218 is kept in an extended position, allowing direct passage through the holes 230 and 222 for sterilization moisture and gasses. The passage of gasses or fluids is depicted by the arrow 242 (at this time, the depending wall 238 is above the level of the holes 230, 222 as viewed in FIG. 10). During the deployment operation, the upper part 218 is moved towards the lower part 220, such that the depending wall 238 nests and slides into the annular gap 228. In so doing, the depending wall passes between the holes 230, 222 in order to seal these from one another and the inside of the chamber 220 from the outside. Further pressing of the upper part 218 into the lower part 216 causes the remaining fluid in the annular gap 228 to be pressurized and to flow into the sealed chamber 244 through the hole 224, thereby to pressurize the valve 26 into a sealing condition. Thus, the valve 26 can perform its sealing function by a simple and effective maneuver by a surgeon or other clinician.

The two parts 216 and 218 can be moved towards one another by pushing, by a screwing action (in which case they would be threadedly coupled to one another) or in any other way. It will be apparent that sufficient pressure for sealing could be achieved with very little movement of the parts 216 and 218 once the holes 230, 222 have been sealed closed.

A friction fitting, adjustable ratchet or latching device, screw thread or any other device may be provided to keep the upper and lower parts in a sealing position relative to one another.

The systems taught herein can provide a much enhanced sealing function compared to prior art systems. Furthermore, as a result of this the valve element does not have to be formed of a compliant material as with existing haemostatic valves. The valve element could equally be formed of a relatively non-compliant material, such as a material commonly used for endovascular balloons, for example polyethylene terephthalate (PET), polyethylene, nylon, PVC, or any other known materials. An advantage of non-compliant materials of this type is that they can be very flexible and have lower coefficients of friction compared to compliant materials.

What is claimed is:

1. A haemostatic valve assembly including a chamber able to be pressurized, an elongate resiliently deformable valve element located within the chamber, a passage through which an elongate element can pass, the valve element being located so as to envelop at least a part of the passage, and a fluid supply for supplying a volume of pressurized fluid to within the chamber, wherein pressurization of the chamber causes the valve element to be biased towards a closed position; wherein the fluid supply includes a source of pressurized fluid external to the chamber, including a variable volume drop bag coupled to the chamber in a closed path, wherein gravity acts on the pressurized fluid from the drop bag, causing the fluid to apply pressure to the valve element and deform the valve element to bias it into a sealing condition against an elongate element therein or to a closed position; the volume of fluid within the valve chamber being self-adjusting so as to provide a substantially constant sealing force at all operating conditions of the valve element, said sealing force being sufficient to seal against leakage around an elongate element passing through the valve without any other means assisting to apply mechanical pressure to seal against leakage around an elongate element passing through the valve.

2. A haemostatic valve assembly according to claim 1, wherein the chamber provides a substantially constant volume for pressurization fluid.

3. A haemostatic valve assembly according to claim 1, wherein that the chamber is or includes a variable volume element.

4. A haemostatic valve assembly according to claim 1, wherein the resiliently deformable valve element is one of: an hourglass and a cylindrical shape.

5. A haemostatic valve assembly according to claim 1, wherein the valve element extends substantially along the entirety of the passage through the chamber.

6. A haemostatic valve assembly according to claim 5, wherein the valve element is fluid-tight to the chamber.

7. A haemostatic valve assembly according to claim 1, wherein the valve extends over only a portion of the passage of the chamber.

8. A haemostatic valve assembly according to claim 7, including at least one securing device for securing the free end of the valve.

9. A haemostatic valve assembly according to claim 8, wherein the or each securing device includes a filament.

10. A haemostatic valve assembly according to claim 1, wherein the valve element is provided with one or more holes into the passage within the chamber.

11. A haemostatic valve assembly according to claim 1, wherein the valve element has a multi-leaflet form.

12. A haemostatic valve assembly including a chamber able to be pressurized, an elongate resiliently deformable valve element located within the chamber, the resiliently deformable valve element being one of; an hourglass and a cylindrical shape, a passage through which an elongate element can pass, the valve element being located so as to envelop at least a part of the passage, and a fluid sealed within the chamber; the assembly including a source of pressurized fluid external to the chamber, wherein fluid is contained within the source of pressurized fluid in a sealed manner, and a coupling for deriving pressure from a patient's blood system the coupling comprising a membrane between the chamber and the source of pressurized fluid external to the chamber wherein the membrane is moveable by the pressurised fluid so as to compress the fluid sealed within the chamber such that it applies pressure to the valve element and deforms the valve element to bias it into a sealing condition against an elongate element therein or to a closed position, the device providing a self-adjusting sealing force on the valve element, said sealing force being sufficient to seal against leakage around an elongate element passing through the valve without any other means assisting to apply mechanical pressure to seal against leakage around an elongate element passing through the valve.

13. A haemostatic valve assembly according to claim 12, wherein the valve element has a multi-leaflet form.

14. A deployment device including a haemostatic valve assembly provided with a chamber able to be pressurized, an elongate resiliently deformable valve element located within the chamber, a passage through which an elongate element can pass, the valve element being located so as to envelop at least a part of the passage, and a fluid supply for supplying a volume of pressurized fluid to within the chamber, wherein pressurization of the chamber causes the valve element to be biased towards a closed position; wherein the fluid supply includes a source of pressurized fluid external to the chamber, including a variable volume drop bag coupled to the chamber in a closed path the pressurized fluid from the drop bag applying pressure to the valve element and deforming the valve element to bias it into a sealing condition against an elongate element therein or to a closed position; the volume of fluid within the valve chamber being self-adjusting so as to provide a substantially constant sealing force at all operating conditions of the valve element, said sealing force being sufficient to seal against leakage around an elongate element passing through the valve without any other means assisting to apply mechanical pressure to seal against leakage around an elongate element passing through the valve.

15. An intravenous treatment assembly including a haemostatic valve assembly provided with a chamber able to be pressurized, an elongate resiliently deformable valve element located within the chamber, a passage through which an elongate element can pass, the valve element being located so as to envelop at least a part of the passage, and a fluid supply for supplying a volume of pressurized fluid to within the chamber, wherein pressurization of the chamber causes the valve element to be biased towards a closed position; wherein the fluid supply includes a source of pressurized fluid external to the chamber, including a variable volume drop bag coupled to the chamber in a closed path the pressurized fluid from the drop bag applying pressure to the valve element and deforming the valve element to bias it into a sealing condition against an elongate element therein or to a closed position; the volume of fluid within the valve chamber being self-adjusting so as to provide a substantially constant sealing force at all operating conditions of the valve element, said sealing force being sufficient to seal against leakage around an elongate element passing through the valve without any other means assisting to apply mechanical pressure to seal against leakage around an elongate element passing through the valve.

* * * * *